US005543555A

United States Patent [19]

Pitt et al.

[11] Patent Number: 5,543,555

[45] Date of Patent: * Aug. 6, 1996

[54] SURFACTANTS AND HYDROPHILIC COLLOID COMPOSITIONS AND MATERIALS CONTAINING THEM

[75] Inventors: Alan R. Pitt, Sandridge; Julian C. Caesar, Stratford; Danuta Gibson, Garston; Trevor J. Wear, South Harrow; David J. Young, Chorleywood, all of England; Scott A. King, Penfield, N.Y.

[73] Assignee: Eastman Kodak Company, Rochester, N.Y.

[ * ] Notice: The term of this patent shall not extend beyond the expiration date of Pat. No. 5,380,628.

[21] Appl. No.: 478,624

[22] Filed: Jun. 7, 1995

Related U.S. Application Data

[62] Division of Ser. No. 198,729, Feb. 18, 1994.

[51] Int. Cl.[6] ........................ C07C 309/04; B01F 17/00; G03C 1/38

[52] U.S. Cl. ........................ 560/151; 252/354; 430/546; 430/631

[58] Field of Search .................................... 430/546, 631, 430/449; 560/151; 106/492, 22; 252/351, 354

[56] References Cited

U.S. PATENT DOCUMENTS

| | | | |
|---|---|---|---|
| 2,949,360 | 8/1960 | Julian | 430/546 |
| 3,948,663 | 4/1976 | Shiba | 430/505 |
| 4,988,610 | 1/1991 | Pitt et al. | 430/449 |
| 5,135,844 | 8/1992 | Bagchi et al. | 430/546 |
| 5,380,628 | 1/1995 | Sawyer et al. | 430/449 |

FOREIGN PATENT DOCUMENTS

93/03420 2/1993 WIPO .

*Primary Examiner*—Janet C. Baxter
*Attorney, Agent, or Firm*—Andrew J. Anderson

[57] ABSTRACT

Surfactants useful as dispersing aids in the preparation of compositions comprising a hydrophilic colloid having hydrophobic particles dispersed therein have the structure

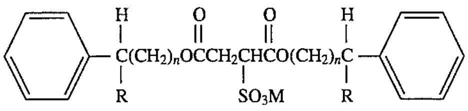

I wherein

R is H or methyl provided that when each n=1, each R is methyl;

M is a cation; and, n is an integer from 1 to 6.

Such surfactants offer coating, photographic property and processing advantages when incorporated in photographic materials comprising a support bearing a plurality of hydrophilic colloid layers including at least one light-sensitive silver halide emulsion layer wherein at least one of the underlying hydrophilic colloid layers of the material contains hydrophobic particles dispersed therein with the aid of the surfactant.

10 Claims, No Drawings

SURFACTANTS AND HYDROPHILIC COLLOID COMPOSITIONS AND MATERIALS CONTAINING THEM

This is a divisional of U.S. application Ser. No. 198,729, filed Feb. 18, 1994, allowed.

FIELD OF INVENTION

The invention relates to surfactants and their use as dispersing aids in the preparation of hydrophilic colloid compositions having hydrophobic particles dispersed therein. Such compositions may be used in the preparation of multilayer photographic materials.

BACKGROUND OF THE INVENTION

A wide variety of surfactants have been described for use in the preparation of photographic materials.

JP56-19042 describes various diester sulfoitaconates as dispersing aids for photographic additives. The two ester linked hydrophobic groups include a number of substituted or unsbstituted alkyl or aryl groups.

U.S. Pat. No. 3,948,663 describes photographic materials containing certain sulfosuccinate surface active agents and refers to their possible use as dispersing aids and coating aids. A specific example of such a surface active agent is sodium dioctyl sulfosuccinate which is commercially available as Aerosol™OT.

W093/03420 describes a method of making fine particle photographic coupler dispersions which comprises forming a dispersion of photographic coupler, coupler solvent and auxiliary coupler solvent in an aqueous gelatin medium containing at least about 1% by weight of an anionic surfactant having a hydrophobicity of 2–10 log P(OH) and washing the dispersion with water for a time sufficient to remove at least one fourth of the surfactant. Anionic surfactants of diverse structures may be employed and included among several named surfactants is diphenylbutyl sodium sulfosuccinate.

A shortcoming of the use of surfactants described in JP56-19042 and U.S. Pat. No. 3,948,663 is the very low surface tension values exhibited by the compounds at concentrations above their critical micelle concentration (CMC). In the simultaneous multilayer coating of hydrophilic colloid layers, it is essential that the surface tension of the top layer is lower than that of any of the underlying layers if it is to remain spread during the coating operation. If one of the underlying lavers has a lower surface tension than the top layer it drives the top layer in from the edges towards the centre of the coating. This is often termed "edge retraction". The larger the surface tension imbalance, the more disruptive is the effect. Large differences can cause retraction of the whole coating pack and general layer inversions. The surface tension of underlying layers in the multilayer coating of photographic materials is often dominated by the surfactant dispersing aid that is used to stabilize the emulsified hydrophobic particles therein e.g. colour couplers and their associated solvents.

When such prior art surfactants are used as dispersing aids for emulsified materials that are incorporated in underlying hydrophilic colloid layers during simultaneous multilayer coating, a constraint is put on the choice of surfactant or surfactant concentration required for the overlying layers i.e. coating latitude is relatively narrow.

Another shortcoming of the use of the surfactants described in JP56-19042 and U.S. Pat No. 3,948,663 as dispersing aids for photographic couplers in hydrophilic colloid compositions is that the photographic properties of such compositions e.g. the liquid dispersion reactivity, can be less than desired.

A further shortcoming of the use of the surfactants described in JP56-19042 and U.S. Pat. No. 3,948,663 as dispersing aids in photographic materials is that they can contribute to foaming during photographic processing, especially in seasoned developers where surfactants have leached out from the material and have built up in concentration.

Problem to be Solved by the Invention

The invention overcomes the coating latitude problem associated with the prior art dipersing aids.

Limitations in the photographic properties of dispersions of photographic couplers in hydrophilic colloids can be overcome.

The invention can reduce the foaming which can occur during the processing of photographic materials containing the prior art dispersing aids.

SUMMARY OF THE INVENTION

The invention provides compounds having the structure

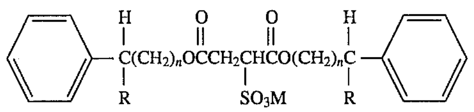

I wherein

R is H or methyl provided that when each n=1, each R is methyl;

M is a cation; and, n is an integer from 1 to 6.

The invention also provides a composition comprising a hydrophilic colloid having hydrophobic particles dispersed therein with the aid of a surfactant having the structure I.

A multilayer photographic material comprises a support bearing a plurality of hydrophilic colloid layers including at least one light-sensitive silver halide emulsion layer wherein at least one of the underlying layers of the material contains hydrophobic particles dispersed therein with the aid of a surfactant having the structure I.

A method of preparing a multilayer photographic material comprises (a) simultaneously coating on a support a plurality of aqueous hydrophilic colloid layers including at least one light-sensitive silver halide emulsion layer wherein at least one of the underlying layers contains hyrophobic particles dispersed therein with the aid of a surfactant having the structure I, and (b) drying the coated layers.

Advantageous Effect of the Invention

By providing aqueous hydrophilic colloid melts with high surface tension minima, the invention enables increased coating latitude.

Improved photographic performance can be achieved with dispersions of a photographic coupler in a hydrophilic colloid. The nature of the improvement depends on the type of coupler dispersion. For example, with a microprecipitated dispersion, the benefits include decreased droplet size, increased liquid dispersion reactivity, and increased Dmax in coated product. With a homogenized dispersion, the benefits include increased liquid dispersion reactivity, and increased shoulder density and contrast in coated product.

Another advantage is reduced foam formation during photographic processing, especially in seasoned developer.

DETAILED DESCRIPTION OF THE INVENTION

In structure I, the cation M is a positively charged atom or group of atoms preferably chosen from alkali metal cations e g. $Na^+$, or ammonium.

Preferred compounds include those wherein each n is from 2 to 4, and each R is H. In a particularly preferred compound, each n is 3, and each R is H.

The compounds may be water soluble or water dispersible.

The compounds may be prepared by the esterification of maleic acid with a phenylalkanol wherein the alkanol has from 3 to 8 carbon atoms. A specific method which can be used in respect of all the compounds is given below in Example 1.

Compositions comprising a hydrophilic colloid having hydrophobic particles dispersed therein may be formed by a process comprising dispersing a hydrophobic material into an aqueous solution of a hydrophilic colloid in the presence of the surface active agent.

For homogenized dispersions, the surface active agent is used preferably in an amount from 0.4 to 1.2, more preferably from 0.6 to 0.9 weight percent based on the weight of the aqueous dispersion.

For microprecipitated dispersions, the surface active agent is used preferably in an amount that provides a molar ratio of surface active agent: hydrophobic material e.g. photographic coupler which is from 1:4 to 2:1.

Regardless of the particular method of preparation, dispersions can be made in accordance with the invention which avoid the coating latitude problems associated with the prior art by using less than about 1 weight percent of the surfactant and without requiring a washing step to remove at least one fourth of the surfactant.

The invention is particularly useful in the preparation of photographic compositions and materials.

In the following discussion of suitable materials for use in the compositions and materials of this invention, reference will be made to *Research Disclosure*, December, 1989, Item 308119, published by Kenneth Mason Publications, Ltd., Dudley Annex, 12a North Street, Emswoth, Hampshire, P010 7DQ, UK. This publication will be identified hereafter by the term *Research Disclosure.*

A number of hydrophobic photographic additives used in light sensitive photographic materials are oil-soluble and are used by dissolving them in a substantially water-insoluble, high boiling point solvent which is then dispersed in an aqueous hydrophilic colloid solution with the assistance of a dispersing aid. Such oil-soluble additives include image forming dye couplers, dye stabilizers, antioxidants and ultraviolet radiation absorbing agents. A typical solvent used to dissolve the additive is aromatic e.g. di-n-butyl phthalate.

Gelatin is the preferred hydrophilic colloid, but other hydrophilic colloids can be used alone or in combination with gelatin.

Suitable methods of preparing photographic dispersions are described in *Research Disclosure* Sections XIV A and XIV B. For example, homogenised oil in aqueous gelatin dispersions of photographic couplers can be prepared by dissolving the coupler in a coupler solvent and mechanically dispersing the resulting solution n an aqueous gelatin solution (see U.S. Pat. No. 2,322,027).

Alternatively, microprecipitated dispersions of photographic couplers prepared by solvent and/or pH shift techniques are becoming more widely used (see references: U.K. Patent No. 1,193,349; Research Disclosure 16468, December 1977 pp 75–80; U.S. Ser. No. 288,922 (1988) by K.Chari; U.S. Pat. Nos. 4,970,139 & 5,089,380 by P.Bagchi; U.S. Pat. No. 5,008,179 by K. Chari, W. A. Bowman & B. Thomas; U.S. Pat. No. 5,104,776 by P. Baghi & S. J. Sargeant) and offer benefits in decreased droplet size and often increased reactivity relative to conventional oil-in-water homogenised dispersions.

Multilayer photographic materials according to the invention comprise one or more underlying layers formed from such compositions.

Preferred multilayer photographic materials include color materials of the type described in *Research Disclosure*, Sections VII A to VII K.

Methods of preparing multilayer photographic materials by simultaneously coating the layers are known. Particular methods are described in *Research Discloure*, Sections XV A and XV B. Such methods include extrusion coating and curtain coating.

The hydrophobic material dispersed in the hydrophilic colloid may be a photographic coupler.

Couplers which form cyan dyes upon reaction with oxidized color-developing agents are described in such representative patents and publications as U.S. Pat. Nos. 2,772,162; 2,895,826; 3,002,836; 3,034,892; 2,747,293; 2,423,730; 2,367,531; 3,041,236; and 4,333,999; and Research Disclosure, Section VII D.

Couplers which form magenta dyes upon reaction with oxidized color developing agents are described in such representative patents and publications as: U.S. Pat. Nos. 2,600,788; 2,369,489; 2,343,703; 2,311,082; 3,152,896; 3,519,429; 3,062,653; and 2,908,573; and *Research Disclosure*, Section VII D.

Couplers which form yellow dyes upon reaction with oxidized and color developing agents are described in such representative patents and publications as: U.S. Pat. Nos. 2,875,057; 2,407,210; 3,265,506; 2,298,443; 3,048,194; and 3,447,928; and *Research Disclosures*, Section VII D.

Couplers which form colorless products upon reaction with oxidized color developing agents are described in such representative patents as: UK Patent No. 861,138; U.S. Pat. Nos. 3,632,345; 3,928,041; 3,958,993; and 3,961,959.

The couplers can be dissolved in a solvent and then dispersed in a hydrophilic colloid. Examples of solvents usable for this process include organic solvents having a high boiling point, such as alkyl esters of phthalic acid (for example, dibutyl phthalate, dioctyl phthalate, and the like), phosphoric acid esters (for example, diphenyl phosphate, triphenyl phosphate, tricresyl phosphate, dioctyl butyl phosphate, and the like) citric acid esters (for example, tributyl acetyl citrate, and the like) benzoic acid esters (for example, octyl benzoate, and the like), alkylamides (for example, diethyl laurylamides, and the like), esters of fatty acids (for example dibutoxyethyl succinate, dioctyl azelate, and the like), trimesic acid esters (for example, tributyl trimesate, and the like), or the like; and organic solvents having a boiling point of from about 30° to about 150° C., such as lower alkyl acetates (for example, ethyl acetate, butyl acetate, and the like), ethyl propionate, secondary butyl alcohol, methyl isobutyl ketone, b-ethoxyethyl acetate, methyl cellosolve acetate, or the like. Mixtures of organic solvents having a high boiling point and organic solvents having a low boiling point can also be used.

As the binder or the protective colloid for the photographic emulsion layers or intermediate layers of the photographic light-sensitive material of the present invention, gelatin is advantageously used, but other hydrophilic colloids can be used alone or together with gelatin.

As gelatin in the present invention, not only lime-processed gelatin, but also acid-processed gelatin may be employed. The methods for preparation of gelatin are described in greater detail in Ather Veis, *The Macromolecular Chemistry of Gelatin*, Academic Press (1964).

As the above-described hydrophilic colloids other than gelatin, it is possible to use proteins such as gelatin derivatives, graft polymers of gelatin and other polymers, albumin, casein, and the like; saccharides such as cellulose derivatives such as hydroxyethyl cellulose, cellulose sulfate, and the like, sodium alginate, starch derivatives, and the like; and various synthetic hydrophilic high molecular weight substances such as homopolymers or copolymers, for example, polyvinyl alcohol, polyvinyl alcohol semiacetal, poly-N-vinylpyrrolidone, polyacrylic acid, polymethacrylic acid, polyacrylamide, polyvinyl imidazole, polyvinylpyrazole, and the like.

In the photographic emulsion layers or other hydrophilic colloid layers of the photographic light-sensitive material of the present invention can be incorporated various surface active agents as coating aids or for other various purposes, for example, prevention of charging, improvement of slipping properties, acceleration of emulsification and dispersion, prevention of adhesion and improvement of photographic characteristics (for example, development acceleration, high contrast, and sensitization), and the like Surface active agents which can be used are nonionic surface active agents, for example, saponin (steroid-based), alkyene oxide derivatives (for example, polyethylene glycol, a polyethylene glycol/polypropylene glycol condensate, polyethylene glycol alkyl ethers or polyethylene glycol alkylaryl ethers, polyethylene glycol esters, polyethylene glycol sorbitan esters, polyalkylene glycol alkylamines or polyalkylene glycol alkylamides, and silicone/polyethylene oxide adducts, and the like), glycidol derivatives (for example, alkenylsuccinic acid polyglyceride and alkylphenol polyglyceride, and the like), fatty acid esters of polyhydric alcohols and alkyl esters of sugar, and the like; anionic surface active agents containing an acidic group, such as a carboxy group, a sulfo group, a phospho group, a sulfuric acid esters group, and a phosphoric acid ester group, for example, alkylcarboxylic acid salts, alkylsulfonic acid salts, alkylbenzenesulfonic acid salts, alkylnaphthlenesulfonic acid salts, alkylsulfuric acid esters, alkylphosphoric acid esters, N-acyl-N-alkyltaurines, sulfosuccinic acid esters, sulfoalkylpolyoxyethylene alkylphenyl ethers, and polyoxyethylene alkylphosphoric acid esters; amphoteric surface active agents, such as amino acids, aminoalkylsulfonic acids, aminoalkylsulfuric acid or aminoalkylphosphoric acid esters, alkylbetaines, and amine oxides; and cationic surface active agents, for example, alkylamine salts, aliphatic or aromatic quaternary ammonium salts, heterocyclic quaternary ammonium salts (for example, pyridinium and imidazolium) and aliphatic or heterocyclic phosphonium or sulfonium salts.

In the photographic emulsion layer of the photographic light-sensitive material used in the present invention, any of silver bromide, silver iodobromide, silver iodochlorobromide, silver chlorobromide and silver chloride may be used as the silver halide.

The light-sensitive silver halide contained in the photographic material can be processed following exposure to form a visible image by associating the silver halide with an aqueous alkaline medium in the presence of a developing agent contained in the medium or the material. Suitable types of photographic processing are described in *Research Disclosures*, Section XIX A to XIX J. Suitable developing agents are described in *Research Disclosures*, Section XX A to XX B.

The following Examples further illustrate the invention.

A number of compounds referred to in the Examples are as follows:

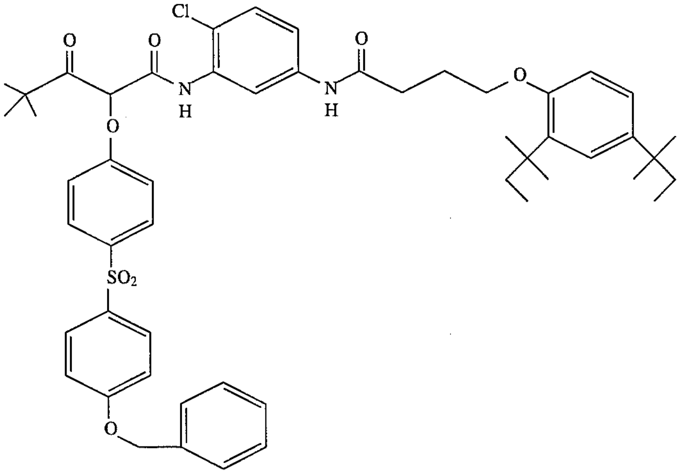

Coupler I

-continued

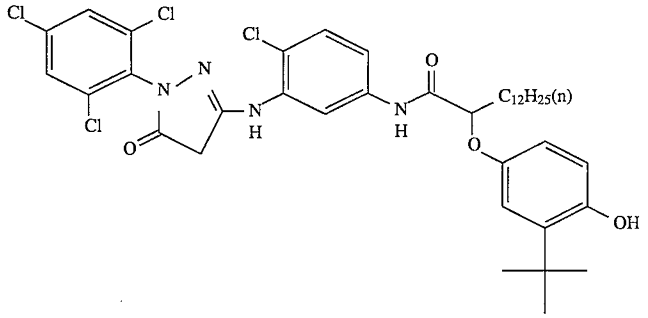

Coupler II

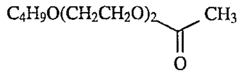

Solvent III

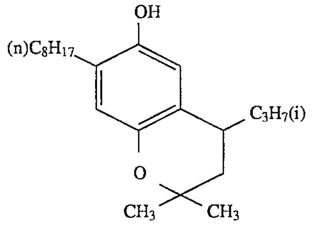

Stabilizer IV

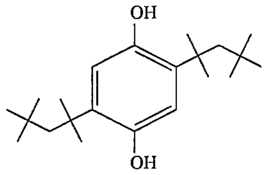

Scavenger V

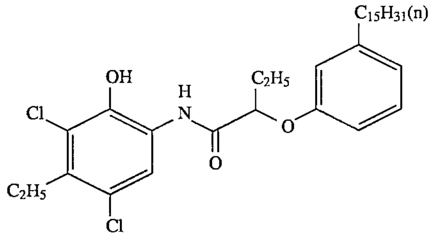

Coupler VI

EXAMPLE 1

Synthesis of sodium di(4-phenylbut-1-yl)sulfosuccinate

All sodium sulfosuccinate surfactants were prepared following the general method outlined below: A solution of maleic anhydride (32.6 g, 0.33 mol), 4-phenyl-1-butanol (100.0 g, 0.66 mol) and concentrated sulfuric acid (1.5 $cm^3$) was suspended in toluene(750 $cm^3$) and refluxed for 16 hours in a flask equipped with a Dean and Stark trap. On cooling, the toluene solution was reduced to ¼ volume at reduced pressure on a rotary evaporator and washed with saturated sodium hydrogen carbonate (2×200 $cm^3$) and then with water (2×200 $cm^3$). The organic layer was dried over magnesium sulfate. and the solvent removed at reduced pressure (15 mmHg, 50° C.) to give an intermediate diester as a clear oil (119.5 g, 95%).

A solution of sodium metabisulfite (65.7 g, 0.34 mol) in water (400 $cm^3$) was added to a solution of this diester (119.5 g, 0.31 mol) in ethanol (400 $cm^3$) and the mixture brought to reflux over 15 minutes. Sodium sulfite (36.0 g, 0.28 mol) was then added portionwise to the mixture over 40 minutes and the reaction then allowed to reflux overnight for convenience. The reaction mixture was evaporated to dryness (15 mm Hg, 50° C.) and then extracted into ethyl acetate (1.5 L, hot) and filtered. The ethyl acetate solution was concentrated and allowed to cool to give the product as a white crystalline solid (139.8 g, step yield 93%, overall yield 87%).

Spectroscopic and 1 Hnmr data was consistent with the proposed product, sodium di (4-phenylbut-1-yl) sulfosuccinate.

EXAMPLE 2

Tables IA and IB compare the surface tension data of the compounds of the invention with commercial examples of dialkyl sulfosuccinate, Aerosol™MA (sodium dihexyl sulfosuccinate), Aerosol™OT (sodium diisooctyl sulfosuccinate) and Aerosol™AY (sodium dipentyl sulfosuccinate). The method used for surface tension measurements is as follows.

The measurement of surface tension of an aqueous solution containing surfactant was measured over a concentration range including the critical micelle concentration using the Wilhelmy technique (Padday, J. F., 2nd Int. Congress of Surface Activity, I, 1, 1957) with a platinum blade. Comparative dynamic surface tension measurements were also determined by the same technique using an overflowing circular weir (ibid.). The average surface age of the solutions in the overflowing weir has been estimated to be of the order of 0.1 seconds.

TABLE IA

Surface Tension (mN/m) of Solutions in Water at 25° C.

| Compounds Tested | Concentration wt % in Water | | | CMC |
|---|---|---|---|---|
| Invention | 0.25% | 0.5% | 1.0% | wt % |
| n = 2, R = Me | 44.9 | 40.3 | 39.0 | 0.64 |
| n = 2, R = H | 37.6 | 37.6 | 37.9 | 0.23 |
| n = 3, R = H | 42.1 | 41.7 | 40.2 | 0.10 |
| n = 4, R = H | — | — | 37.5 | — |

TABLE IB

Surface Tension (mN/m) of Solutions in Water at 25° C. (Trade Literature)

| Compounds Tested | Concentration wt % in Water | | | CMC |
|---|---|---|---|---|
| Comparisons | 0.25% | 0.5% | 1.0% | wt % |
| Aerosol OT | 27.5 | 26.0 | 26.0 | ~0.07 |
| Aerosol MA | 38.2 | 30.8 | 27.8 | 0.6–0.7 |
| Aerosol AY | 41.6 | 35.2 | 29.2 | 0.9–1.2 |

Tables IA and IB show clearly that once the concentrations of the surfactants approach or go beyond their CMC where surface tension values tend to plateau, the compounds of this invention exhibit much higher values of surface tension than the corresponding dialkyl equivalents. Equivalents denote compounds of similar CMC. On comparing equivalent compounds at such concentrations, the materials of this invention show surface tension values that are 10–14 mN/m higher.

Tables IIA and IIB show similar data to Tables IA and IB, but the measurements were conducted in solutions containing 7% deionised Type IV bone gelatin in water at 40° C. to simulate a coating melt.

TABLE IIA

Surface Tension (mN/m) of Solutions in 7% Deionised Type IV Bone Gelatin Water at 40° C. (Compounds of This Invention)

| Compounds Tested | Wt % Concentration in 7% Deionised Gelatin solution | | | CMC |
|---|---|---|---|---|
| Invention | 0.03% | 0.10% | 0.30% | wt % |
| n = 2, R = Me | 49.4 | 44.9 | 41.8 | ~0.3 |
| n = 2, R = H | 49.5 | 44.2 | 43.3 | ~0.1 |
| n = 3, R = H | 43.2 | 42.8 | 42.8 | ~0.03 |
| n = 4, R = H | 42.1 | 41.7 | 40.7 | ~0.01 |

In the following Table, the comparison compounds are sulfosuccinates having the formula

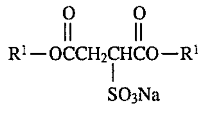

TABLE IIB

Surface Tension (mN/m) of Solutions in 7% Deionised Type IV Bone Gelatin Water at 40° C. (Comparison Compounds)

| Compounds Tested | Wt % Concentration in 7% Deionised Gelatin solution | | | CMC |
|---|---|---|---|---|
| Comparisons | 0.03% | 0.10% | 0.30% | wt % |
| Aerosol OT | 29.2 | 28.9 | 28.7 | ~0.01 |
| Aerosol MA | 41.9 | 36.3 | 31.4 | ~0.1 |
| $R^1$ = n-hexyl | 37.0 | 32.0 | 30.0 | ~0.1 |
| $R^1$ = n-pentyl | 46.0 | 39.9 | 34.4 | ~1.3 |

Tables IIA and IIB also show clearly that once the concentrations of the surfactants approach or go beyond their CMC in aqueous gelatin solution, the compounds of this invention still exhibit much higher values of surface tension than the corresponding dialkyl equivalents. On comparing equivalent compounds at such concentrations, the materials of this invention again show surface tension values that are 10–14 mN/m higher.

In general therefore, the materials of this invention offer the advantage of relatively high surface tension minima coupled with reasonably low CMCs (up to 0.3 weight % in 7% gelatin in water) in situations where low values are undesirable, e.g. in underlying layers during simultaneous multilayer coating.

EXAMPLE 3

Increased Coating Latitude Using Materials of Invention as Dispersing Aid in Underlying Layers during Simultaneous Multilayer Coating:

To show that the compounds of this invention permit a wider coating latitude when used as dispersing aids in the underlying layer of a simultaneous two, layer coating, the following format was coated at 15 m/min at 40° C. with a range of different surfactants:

| | |
|---|---|
| TOP LAYER coated at 10.8 ml/$m^2$ (1 ml/$ft^2$) | 10% type IV regular bone gelatin containing 0.3 wt % surfactant and a blue dye marker. |
| BOTTOM LAYER coated at 59 ml/$m^2$ (5.5 ml/$ft^2$) | coupler dispersion (coupler I or II) diluted to 4% gelatin by weight with water containing a red dye marker. |

12.7 cm (5 ins) wide polyethylene terephthalate film base (suitably subbed to give good adhesion to gelatin)

Bottom layer:

A dispersion of a colour coupler was made according to the following recipes:

2 kg Dispersion of Coupler I:

258 g of coupler I was dissolved in a mixture of 65 g di-n-butyl phthalate and 65 g of solvent III at 145° C. to make Solution A. 176 g of gelatin was dissolved in 1354 g of water containing 17.6 g of dispersing aid (surfactant under test) and 31 g of propionic acid/sodium proprionate preservative to make Solution B After heating Solution B to 80° C., solution A was added to Solution B and the whole mixture was immediately homogenised for 5 minutes at 10,000 rpm with a Kinematica Polytron homogeniser fitted a 35 mm diameter head.

1.7 kg Dispersion of Coupler II:

149 g of coupler II was dissolved in a mixture of 58.5 g di-n-butyl phthalate, 22.3 g of solvent III, 79.1 g. of stabiliser IV and 14.9 g of scavenger V at 145° C. to make Solution C. 149 g of gelatin was dissolved in 1180 g of water containing 16.4 g of dispersing aid (surfactant under test) and 32.7 g of propionic acid/sodium propionate preservative to make Solution D. After heating Solution D to 80° C., solution C was added to Solution D and the whole mixture was immediately homogenised for 5 minutes at 10,000 rpm with a Kinematica Polytron homogeniser fitted with a 35mm diameter head.

The coupler dispersion, which contained approximately 9% gelatin by weight, was then diluted at 40° C. to a gelatin content of 4 wt % with water which contained a red dye marker. The resulting mixture was used for the bottom layer of a two layer hopper coating as illustrated above.

Thus a range of bottom layer coating melts were made which differed in the dispersion component, the major difference being the dispersing aid (surfactant) used. The main objective was to compare four diarylalkyl sulfosuccinate dispersing aids of this invention with two commercial dialkyl sulfosuccinate dispersing aids and the commercial surfactant Alkanol™XC (sodium triisopropyl naphthalene sulphonate). Two types of coupler, I and II, were used for making the coupler dispersions. It should be noted for each coupler used that the comparisons of surfactants were between compounds of similar hydrophilic-lipophilic balance, i.e. of similar CMC.

Top Layer:

Four different surfactants were selected for the top layer coating aid to produce a range of characteristic values of minimum surface tension, 25.5–37.2 mN/m. A working concentration of 0.3% was chosen to ensure that the surfactants were being used well beyond their CMC in order that the surface tensions of their respective solutions under dynamic conditions were very similar to those under static conditions and therefore essentially at a characteristic plateau value. The method used for estimating a dynamic value of surface tension is described Example 2. The materials chosen are listed in the following table together with representative surface tension data.

TABLE III

| Surface Tension Data | | |
|---|---|---|
| Surfactant (0.3 wt % Concentration in 7% by wt Type IV Bone Gelatin in Water + Blue Dye | Dynamic Surface Tension mN/m | Static Surface Tension mN/m |
| Aerosol OT (AOT) | 25.5 | 25.5 |
| Triton X-100 (TX100) | 30.5 | 30.2 |
| Texofor FN15 (TFN15) | 34.7 | 34.4 |
| SDS | 37.3 | 37.2 |

Triton ™ X100 is t-octylphenyl polyethyleneoxide (9.5 moles).
Texofor ™ FN15 is nonylphenyl polyethyleneoxide (15 moles).
SDS is sodium dodecyl sulphate.

A complete 4×7 matrix of two layer coatings were made, coating the four types of top layer over the seven types of bottom layer. The dried coatings were then examined to determine whether the top layer had coated successfully over the underlying layer. The coating was deemed successful (OK) if the blue top layer had remained satisfactorily spread over the full width of the coating, and deemed unsuccessful if the bottom layer had caused the top layer to retract from either the edges or if there was multicratering in the middle of the coating due to the bottom layer pushing through to the surface. With the red dye in the lower laver and the blue dye in the upper layer, it was extremely clear when the coating was unsuccessful. Table IV summarises the coating results taken from representative strips:

TABLE IV

| | Coating Results - Different Surfactants in Top Layer | | | |
|---|---|---|---|---|
| Dispersing | Top Layer Surfactant | | | |
| Aid used: (in bottom layer dispersion component) | AOT Surface Tension 25.5 mN/m | TX100 Surface Tension 30.5 mN/m | TFN15 Surface Tension 34.7 mN/m | SDS Surface Tension 37.3 mN/m |
| n = 2, R = Me (using coupler I) | OK | OK | OK | OK |
| n = 2, R = H (using coupler I) | OK | OK | Slight fine multiple cratering | Slight edge retraction 1–2 craters |
| n = 3, R = H (using coupler II) | OK | OK | OK | OK |
| n = 4, R = H (using coupler II) | OK | OK | OK | OK |
| Aerosol MA (using coupler I) | OK | Slight edge retraction 40 × 8 mm large crater | Severe retraction of both layers and multiple cratering | Total retraction of top layer into fine stripes |
| Aerosol OT (using coupler II) | OK | Severe retraction of both layers and multiple large cratering | Severe retraction of both layers and multiple large cratering | Total retraction of top layer and >50% retraction of bottom layer |
| Alkanol XC (using coupler II) | OK | OK | 3–4 mm of edge retraction plus longitudinal break-through and cratering | Severe retraction of both layers and large cratering |

The above results from the two layer coatings clearly show that there is a large increase in coating latitude when the surfactants of this invention are used as the dispersing aids for dispersions in underlying layers during multi-layer coating relative to the comparison compounds. As previously explained and demonstrated here, this means the use of the dispersing aids of this invention puts less constraint upon the choice of surfactant coating aid required in the top layer for good coating. Logically therefore, there should also be less constraint upon the concentration of a coating aid required to give good coating. This aspect is demonstrated in Table V where Aerosol™OT was used as the coating aid in the top layer over a range of concentrations, using the same coating conditions as before.

TABLE V

| Dispersing Aid used: (in bottom layer dispersion component) | Coating Results - Different Concentrations of Coating Aid AOT in Top Layer / Top Layer Surfactant | | | |
|---|---|---|---|---|
| | AOT Concentration 0.02% | AOT Concentration 0.03% | AOT Concentration 0.05% | AOT Concentration 0.07% |
| Invention | | | | |
| n = 2, R = H (using coupler I) | OK | OK | OK | OK |
| n = 3, R = H (using coupler II) | OK | OK | OK | OK |
| Comparison Compounds | | | | |
| Aerosol MA (using coupler I) | Retraction from edges and longitudinal break-through of bottom layer | Retraction from edges and longitidunal break-through of bottom layer | OK | OK |
| Aerosol OT (using coupler II) | Retraction of both layers and multiple cratering | Edge retraction and multiple longtidinal coating breaks | Slight edge retraction of top layer | Very slight edge retraction of top layer |

EXAMPLE 4

Photographic Benefits with Microprecipitated Dispersions Increased dispersion reactivity.

Microprecipitated dispersions of photographic couplers, prepared by solvent and/or pH shift techniques are becoming more widely used and offer benefits in decreased droplet size and often increased reactivity relative to conventional oil-in-water homogenised dispersions. When microprecipitated dispersions are prepared using the compounds of this invention, these benefits are increased.

The microprecipitated dispersions were made according to the following method:

The coupler (20 g) was dissolved in a mixture of propan-1-ol (40 g) and 20% sodium hydroxide solution (5 g) at 60° C. and poured into a solution of surfactant (weight equimolar with coupler) and polyvinylpyrrolidone (10 g) in water (600 g). The resulting micellar solution was reduced to pH 6.0 by the dropwise addition of 15% propanoic acid, to form the crude microprecipitated dispersion which was then dialysed through Amicon hollow fibre ultrafiltration cartridges and concentrated to a fifth of its volume.

The liquid dispersion reactivity measurements were made according to the following method. Particle size was measured by photon correlation spectroscopy.

The method used is similar to that described by Bagchi in U.S Pat. Nos: 4,970,139; 5,089,380 and 5,104,776. A sample of the dispersion was mixed with a developer solution which contained sodium sulphite, CD-3 developer and EDTA. This was mixed with an activator solution which contained the oxidant sodium persulfate, and a buffer of sodium carbonate and sodium bicarbonate, which brought the pH of the final solution to 10.1 (close to that of processing solutions). The concentrations of oxidant and coupler are much greater than that of the developer. The effect of this is that the oxidant generates oxidised developer which then reacts with the coupler (or with the competing sulfite) to form image dye and side products. The optical density of the dye was then read spectrophotometrically so that for a known dye extinction coefficient, the concentration of the dye could be derived.

If the coupling reaction is treated as a homogeneous, single phase reaction the kinetics of the coupling reaction can be calculated. The coupling reaction and the competing reaction of sulphite with oxidised developer are both assumed to be second order. Remembering that coupler and oxidant concentrations are greater than that of developer, the following expression is derived for the rate constant of the coupling reaction, $k_1$ which is used as a measure of liquid dispersion reactivity:

$$k_1=k_2 \ln [a/(a-x)]/\ln [b/(b-c+x)]$$

where $k_2$ is the sulfonation rate constant (previously calculated), a is the coupler concentration, b is the sulfite concentration, c is the developer concentration and x is the concentration of dye.

TABLE VI

Microprecipitated dispersions of Coupler VI data.

| SURFACTANT (dispersing aid) | Liquid Dispersion Reactivity | Mean Particle Diameter (nm) | Comment |
|---|---|---|---|
| SDS | 9545 | 20.3 | comparison |
| SDBS | 5200 | 25.8 | " |
| Aerosol OT | 4500 | 66.0 | " |
| Aerosol MA | 4575 | 21.6 | " |
| Aerosol AY | 4220 | 20.9 | " |
| TPE-STC | 1730 | 19.2 | " |
| TPME-STC | 203 | 20.9 | " |
| n = 4, R = H | 15100 | 13.0 | invention |
| n = 3, R = H | 14425 | 8.9 | " |
| n = 2, R = H | 10130 | 18.5 | " |
| n = 1, R = Me | 7555 | 17.8 | " |
| n = 1, R = H | 4155 | 20.3 | comparison |

The above results show clearly that the compounds of this invention:

(i) Increase liquid dispersion reactivity as hydrophobic chain length increases. (Note: phenyl propyl is minimum chain length to give increased reactivity thus demonstrating why shorter chains such as phenylethyl lie outside the invention);

(ii) Enhance liquid dispersion reactivity relative to the aliphatic (i.e. non-phenyl ending) sulfosuccinates;

(iii) Boost liquid dispersion reactivity relative to other commonly available anionic dispersing aids, such as sodium dodecyl sulphate (SDS) and sodium dodecylbenzene sulphonate (SDBS);

(iv) Increase liquid dispersion reactivity relative to the try-chain phenyl-ended sulphonates, such as TPE-STC (tri-2-phenylethyl sulfotricarballylate) and TPME-STC (tri-2-phenyl-2-methylethyl sulfotricarballylate) (U.S. Pat. No. 4,988,610), thus demonstrating that the 2 hydrophobic chain geometry of the materials of this invention is critical to their performance;

(v) Decrease particle size, especially with the longer hydrophobic chain examples of the invention, relative to other anionic surfactants, such as SDS, SDBS, aliphatic sulfosuccinates and phenyl-ended sulfotricarballylates.

Increased Dmax

When coatings are made of the most reactive microprecipitated dispersions, the examples of the invention show the highest Dmax.

Monochrome coatings of the microprecipitated dispersions were made according to the procedures outlined.

A monochrome bilayer format was used for the photographic evaluation of the coupler dispersions:

| | | |
|---|---|---|
| Layer 2 | Gelatin | 1.614 $g/m^2$ |
| | Alkanol XC | 21.5 $mg/m^2$ |
| | BVSME | 64.0 $mg/m^2$ |
| Layer 1 | Gelatin | 1.614 $g/m^2$ |
| | Coupler VI | 0.836 $mmoles/m^2$ |
| | Silver (as chloride emulsion) | 239.0 $mg/m^2$ |
| Support | Resin-coated paper | |

The two layers were coated simulatneously.

The coatings were exposed to white light for 0.1 s through a 21 step 0.15 logE increment tablet and processed in standard RA-4 chemistry. Reflection Dmax of each coating was measured using an X-Rite model 414 reflection densitometer. The results were as follows:

TABLE VII

Coatings of Coupler VI microprecipitated dispersions.

| SURFACTANT | Dmax | Comment |
|---|---|---|
| SDS | 2.99 | comparison |
| SDBS | 2.73 | comparison |
| n = 3, R = H | 3.39 | invention |
| n = 2, R = H | 3.19 | invention |
| n = 1, R = H | 2.71 | comparison |

Table VII shows:

(i) Dmax increases with increasing hydrophobic chain length for the materials of the invention;

(ii) Higher Dmax-are obtained with the longer chain length compounds of this invention than for the commonly available anionic dispersing aids such as SDS and SDBS;

(iii) The advantages of higher Dmax are not seen with the short phenyl-ended sulfosuccinates which are outside the scope of this invention.

Photographic Benefits with Homogenised Oil-in-Aqueous Gelatin Dispersions of Colour Couplers Increased contrast and shoulder density. Traditionally colour couplers are dissolved in a high-boiling, water-insoluble solvent and mechanically dispersed in an aqueous gelatin solution containing surfactant to facilitate dispersion. Mean droplet sizes are usually significantly larger (typically, 0.2 μm) than those produced by microprecipitation techniques (typically, 0.02 μm).

The homogenised dispersions were made according to the following technique:

A dispersion was made of the following general formula:

| | |
|---|---|
| Coupler VI | 11.7% |
| di-n-butylphthalate | 3.9% |
| gel | 9.5% |
| water & surfactant | 74.8% |

Coupler VI was dissolved in red in di-n-butyl phthalate and heated at 140° C. until the coupler had completely dissolved. Gelatin was dissolved in water and heated to 70° C. Surfactant was added to the gelatin solution at a rate of 0.1 mole equivalent to coupler. The coupler solution was then added to the gelatin solution and homogenised for 3 minutes using a Kinematica Polytron set at 10,000 rpm and then passed (twice) through a Microfluidics Microfluidiser (model no. 110E) which was run at 68.95 MPa (10,000 psi) pressure and a water bath temperature of 75° C.

The coatings were made as described above and were exposed to white light for 0.1s through a 21 step 0.15 logE increment tablet and processed in standard RA-4 chemistry. The contrast, Dmax, Dmin and shoulder densities were measured using an X-Rite model 414 reflection densitometer and are shown in Table VIII In the following Table, the comparison surfactant types are as follows:

Type A—Sulfonate

Type B—Sulfosuccinate

Type C—Sulfoitaconate having the formula

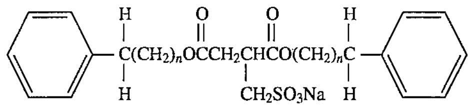

Type D—Sulfoglutaconate having the formula

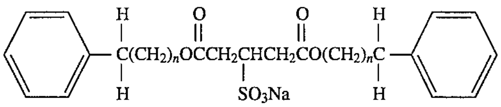

TABLE VIII

Measurements of coated dispersions of coupler VI made with different surfactants.

| Surfactant | Contrast ±0.06 | Shoulder ±0.03 | Dmax ±0.02 | Dmin ±0.003 | Comment |
|---|---|---|---|---|---|
| Type A | 3.45 | 1.91 | 2.32 | 0.111 | comp |
| SDBS | | | | | |
| Type B | | | | | |
| A-OT | 3.56 | 1.94 | 2.42 | 0.110 | comp |
| n = 4, R = H | 3.72 | 1.99 | 2.40 | 0.112 | inv |
| n = 3, R = H | 3.77 | 2.01 | 2.51 | 0.113 | inv |
| n = 2, R = H | 3.80 | 2.00 | 2.52 | | inv |
| n = 1, R = Me | 3.73 | 2.00 | 2.44 | 0.113 | inv |
| n = 1, R = H | 3.28 | 1.87 | 2.23 | 0.109 | comp |
| n = 0, R = H | 3.39 | 1.89 | 2.36 | 0.112 | comp |
| Type C | | | | | |
| n = 0 | 3.63 | 1.95 | 2.35 | 0.114 | comp |
| n = 1 | 3.63 | 1.95 | 2.47 | 0.110 | comp |
| n = 2 | 3.59 | 1.93 | 2.40 | 0.112 | comp |
| n = 3 | 3.34 | 1.86 | 2.30 | 0.115 | comp |
| Type D | | | | | |
| n = 0 | 3.46 | 1.92 | 2.31 | 0.114 | comp |
| n = 3 | 3.56 | 1.95 | 2.39 | 0.109 | comp |

For homogenised dispersions of coupler VI, the materials of the invention clearly show:

(i) Increased contrast and increased shoulder density relative to aliphatic, non phenyl-ended sulfosuccinates such as Aerosol OT; conventional anionic surfactants such as SDBS ω-arylalkyl phenyl-ended sulfoitaconates and sulfoglutaconates; and the shorter chain phenyl-ended sulfosuccinates which are outside the scope of this invention;

(ii) The shorter chain phenyl-ended sulfosuccinates which are outside the scope of this invention also show significantly lower Dmax emphasising the importance of chain length for the materials of this invention;

(iii) No significant Dmin penalty.

In summary, the phenyl-ended sulfosuccinate dispersing aids of this invention show advantages over a wide variety of chemically similar materials when used in the photographic context described.

Increased liquid dispersion reactivity

Dispersions of couplers I and II were made according to the procedures shown in Example 3. The liquid dispersion measurements were made as described above and are presented in Table IX.

TABLE IX

| Liquid dispersion data for homogenised dispersions of couplers I and II. | | | |
|---|---|---|---|
| | Liquid dispersion reactivity rate constants | | |
| Surfactant | Coupler I | Coupler II | Comments |
| Aerosol OT | 1820 | 12600 | comparison |
| Alkanol XC | 3920 | 10230 (±390) | comparison |
| n = 2, R = H | 4690 | 19100 (±140) | invention |
| n = 3, R = H | 4400 | 15800 | invention |

Table IX clearly shows that for coupler I and coupler II dispersions, the materials of the invention boost liquid dispersion reactivity relative to aliphatic, non-phenyl ended sulfosuccinates, such as Aerosol™OT, and a conventional anionic surfactant, such as Alkanol™XC.

EXAMPLE 5

Low Foaming in Developer

Foaming can cause serious problems during photographic processing especially in seasoned developers where surfactants have leached out from the photographic product and built up in concentration. These foams can cause solution overflow, solution loss, uneven development and solution carry over into successive processing tanks.

To demonstrate that one of the preferred materials of this invention showed a lower propensity to foaming, tests were conducted with a simulated seasoned developer based on colour developer ECP-2b using the Ross-Miles foam test.

The test was first devised by Ross and Miles (Ross, J. and G D Miles, Am. Soc. for Testing Materials, Method D1173-53, Philadelphia, Pa. 1953; Oil and Soap 18, 99,1941). This test involves placing some solution in both a lower and upper reservoir; the solution passes out of the upper reservoir through a specific orifice (2.9 mm i.d.), drops freely through a specified distance (initially 90 cm), then splashes into the lower reservoir. The foam so formed is measured immediately after the upper reservoir is empty, then again 5 minutes later. Foam stability is then assessed as the percentage of the height remaining after 5 minutes relative to-the initial height of the foam. Obviously the lower the percentage the lower the foam stability.

To simulate seasoned developer, solutions of ECP-2b were made up at 37–38° C. such that each solution contained 0.006 wt % gelatin and 0.002 wt % surfactant. Each surfactant was tested independently in this format.

In the following Table, Foam Stability is defined as Foam (5 min)/Foam (0 min)×100%.

TABLE X

| Ross-Miles Foam Tests | | | |
|---|---|---|---|
| Surfactant | Foam (0 min) | Foam (5 min) | Foam stability |
| Comparisons | | | |
| Control (none) | 21 mm | 1 mm | 5 |
| Aerosol OT | 60 mm | 59 mm | 98 |
| Alkanol XC | 57 mm | 53 mm | 93 |
| Olin 10G | 35 mm | 31 mm | 89 |
| FT248 | 38 mm | 29 mm | 76 |
| Invention | | | |
| n = 3, R = H | 37 mm | 15 mm | 41 |

Olin ™ 10G is nonylphenyl decaglycidol
FT248 is tetraethylammonium perfluorooctane sulphonate.

Table X demonstrates that one of the preferred materials of this invention(n=3, R=1) produces significantly less foam in the simulated seasoned developer than the corresponding aliphatic sulfosuccinate, Aerosol™OT, and significantly less foam than examples of other surfactants that may be found in photographic products, e.g. Alkanol™XC, Olin 10G and FT248

What is claimed is:

1. A compound having the structure

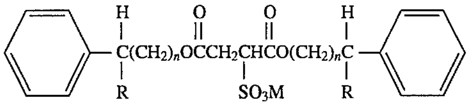

I wherein

R is H or methyl provided that when each n=1, each R is methyl;

M is a cation; and, n is an integer from 1 to 6.

2. A compound according to claim 1 wherein each n is an integer from 2 to 4, and each R is H.

3. A compound according to claim 1 wherein each n is 3, and each R is H.

4. A compound according to claim 1 wherein M is an alkali metal ion.

5. A composition comprising a hydrophilic colloid having hydrophobic particles dispersed therein with the aid of a surfactant having the structure

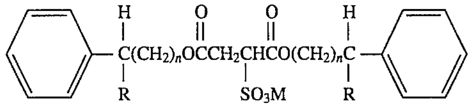

I wherein

R is H or methyl provided that when each n=1, each R is methyl;

M is a cation; and, n is an integer from 1 to 6.

6. A composition according to claim 5 wherein each n is an integer from 2 to 4, and each R is H.

7. A composition according to claim 5 wherein each n is 3, and each R is H.

8. A composition according to claim 5 wherein M is an alkali metal ion.

9. A composition according to claim 5 wherein the hydrophilic colloid is gelatin.

10. A composition according to claim 5 wherein the hydrophobic particles comprise a photographic coupler.

* * * * *